United States Patent [19]

Okisaki et al.

[11] Patent Number: 4,935,562
[45] Date of Patent: Jun. 19, 1990

[54] METHOD FOR PRODUCING 4,4'-DIBROMOBIPHENYL

[75] Inventors: Fumio Okisaki, Shin-nanyo; Masashige Kubo, Tokuyama; Satoshi Fujii, Shin-nanyo; Kiyotaka Oyama, Hikari, all of Japan

[73] Assignee: Tosoh Corporation, Shin-nanyo, Japan

[21] Appl. No.: 281,037

[22] Filed: Dec. 7, 1988

[30] Foreign Application Priority Data

Dec. 7, 1987 [JP] Japan ................................. 62-307569

[51] Int. Cl.$^5$ ............................................. C07C 17/12
[52] U.S. Cl. .................................... 570/210; 570/206; 570/208
[58] Field of Search ........................ 570/206, 208, 210

[56] References Cited

U.S. PATENT DOCUMENTS 1,835,754 12/1931 Britton et al. .
3,285,965 11/1966 Jenkner ............................. 570/206

OTHER PUBLICATIONS

N. Rabjohn et al.: "Organic Synthesis", vol. 4, revised edition of annual vols. 30–39, pp. 256–259, John Wiley & Sons, Inc., New York, US.

*Primary Examiner*—Werren B. Lone
*Attorney, Agent, or Firm*—Oblon, Spivak, McClelland, Maier & Neustadt

[57] ABSTRACT

A method for producing 4,4'-dibromobiphenyl, which comprises reacting biphenyl and from 2 to 3 mol times, relative to biphenyl, of bromine in a halogenated hydrocarbon solvent in the presence of a catalyst which is a simple substance of an element selected from the group consisting of antimony, titanium, tin and zinc, or a compound of the element.

7 Claims, No Drawings

METHOD FOR PRODUCING 4,4'-DIBROMOBIPHENYL

The present invention relates to a process for producing 4,4'-dibromobiphenyl (hereinafter referred to simply as 4,4'-DBBP). 4,4'-DBBP is useful as starting meterial for biphenyl-4,4'-diol (hereinafter referred to simply as 4,4'-BPDO). 4,4'-BPDO is useful as a monomer for engineering plastics, as an antioxidant, or as an intermediate for dyes.

Heretofore, the following methods have been proposed for the bromination of biphenyl (hereinafter referred to simply as BP) with bromine. Namely, (1) a method wherein carbon disulfide is used as a solvent (Journal of the Chemical Society, vol. 47, p. 586 (1885)), (2) a method wherein acetic acid is used as a solvent (Chemische Berichte, vol. 44, p. 1087 (1911)), (3) a method wherein sulfuric acid is used as a solvent (Journal of the American Chemical Society, vol. 43, p. 3061 (1921)) and (4) a method wherein sulfur dioxide is used as a solvent (published German Application No. 1930594 (1970)) are known. Further, Organic Synthesis Collective Volume, vol. 4, p. 256 discloses a method wherein bromine vapor is reacted to fine BP powder. However, these methods have problems such that the reaction time is long, bromine is consumed by the reaction of bromine with the solvent, the yield is low, and the solvent is difficult to handle due to the physical properties thereof.

On the other hand, Japanese Unexamined Patent Publication No. 64532/1980 discloses a method wherein bromination is conducted in the absence of a catalyst by using as a solvent a halogenated hydrocarbon or nitrated hydrocarbon having a dielectric constant of at least 6.5. As such a solvent, 1,2-dichloroethane, 1,1-dichloroethane, 1,1,2,2-tetrachloroethane, 1,2-dichloropropane, nitroethane, o-dichlorobenzene and nitrobenzene are exemplified in the Examples.

The method wherein a nitro compound is used as a solvent, good results are obtainable with respect to the yield and the selectivity. However, such a method has a problem as an industrial method, since vigorous heat-generation takes place even when bromine is dropwise added at room temperature to the solvent containing biphenyl, and in a large scale operation, it is likely that the control of the reaction will be difficult. On the other hand, when a halogenated hydrocarbon is used as a solvent, no such vigorous heat-generation takes place. However, in this case, the reaction tends to terminate with monobromobiphenyl (hereinafter referred to simply as BBP) and hardly proceed to dibromobiphenyl (hereinafter referred to simply as DBBP), whereby both the selectivity and the yield will be low.

Further, in the case of a bromination reaction wherein a strong Lewis acid such as ferric chloride or aluminum chloride is used as a catalyst, there is a problem that poly-brominated products such as tribromobiphenyl (hereinafter referred to simply as TrBBP) and tetrabromobiphenyl (hereinafter referred to simply as TBBP) are likely to form, whereby the yield and the selectivity for 4,4'-DBBP tend to be low.

Under these circumstances, the present inventors have conducted extensive researches and as a result, have found it possible to produce 4,4'-DBBP from BP in good yield and with high selectivity peculiarly when certain specific catalyst and solvent are employed and bromine is used in an amount within a certain specific range as the bromination agent. The present invention has been accomplished on the basis of this discovery.

The present invention provides a method for producing 4,4'-dibromobiphenyl, which comprises reacting biphenyl and from 2 to 3 mol times, relative to biphenyl, of bromine in a halogenated hydrocarbon solvent in the presence of a catalyst which is a simple substance of an element selected from the group consisting of antimony, titanium, tin and zinc, or a compound of the element.

Now, the present invention will be described in detail with reference to the preferred embodiments.

The catalyst used in the method of the present invention is a simple substance of an element selected from the group consisting of antimony, titanium, tin and zinc, or a compound of such an element, such as a halide, oxide, hydroxide, or inorganic or organic salt of the element. These catalysts may be used alone or may be used in combination as a mixture of two or more. The catalyst is preferably a halide, and a chloride is most suitable in view of the yield, selectivity, availability and stability.

The catalyst is used preferably in an amount of from 0.1 to 10 mol % relative to BP. If the amount is less than 0.1 mol %, no substantial effect as the catalyst is obtainable. On the other hand, if the amount exceeds 10 mol %, no additional effects will be obtained due to the increased amount, and the selectivity tends to be rather low, such being undesirable. Further, it is likely that the quality of 4,4'-DBBP deteriorates due to an inclusion of the catalyst.

The amount of bromine used in the method of the present invention is from 2 to 3 mol times relative to BP. If the amount is less than 2 mol times, the reaction tends to terminate with BBP, and if the amount exceeds 3 mol times, poly-brominated products such as TrBBP and TBBP tend to increase. In each case, the yield of 4,4'-DBBP decreases, such being undesirable.

The halogenated hydrocarbon used as the solvent in the method of the present invention may be a halogenated aliphatic hydrocarbon or a halogenated aromatic hydrocarbon. For example, the solvent includes chlorobenzene, o-dichlorobenzene, m-dichlorobenzene, dichloromethane, chloroform, carbon tetrachloride, 1,1'-dichloroethane, 1,2-dichloroethane, 1,1,1-trichloroethane, 1,1,2-trichloroethane, 1,1,2,2-tetrachloroethane, tetrachloroethylene, 1-chloropropane, 2-chloropropane, 1,2-dichloropropane and 1,3-dichloropropane.

In the method of the present invention, the reaction operation comprises dropwise adding bromine or its solution while stirring a halogenated hydrocarbon solution of BP containing the above-mentioned catalyst. The initial concentration of BP is usually from 10 to 100 wt/vol %. If the initial concentration is lower than this range, the reaction tends to be slow. On the other hand, if the concentration exceeds this range, not only the yield does not substantially improve, but also the decrease in the stirring efficiency due to the precipitation of 4,4'-DBBP crystals will be substantial, whereby the control of the reaction will be difficult.

Bromine may be dropwise added without dilution or in the form of a solution. In the case where it is dropwise added in the form of a solution, at least one of the solvents selected from the group of the solvents mentioned above as the solvents for the reaction may be used as a solvent for diluting bromine. It is preferred to employ the same solvent as used for the reaction with a view to recycling the solvent.

In the present invention, bromine or its solution is dropwise added to the BP solution having a temperature within a range of from 0 to 40° C. If the temperature is lower than 0° C., the solubility of BP is low, and a large amount of the solvent will be required. On the other hand, if the temperature exceeds 40° C., the bromination reaction tends to proceed rapidly, whereby the formation of poly-brominated products such as TrBBP and TBBP increases, whereby the yield of 4,4'-DBBP decreases. It is preferred to heat the system after the dropwise addition of bromine or its solution, whereby the yield of 4,4'-DBBP will be improved and the efficiency for the utilization of bromine will be improved. The heating temperature for this purpose is within a range of from 30 to 80° C.

4,4'-DBBP formed by the reaction, precipitates as crystals in the system, and it can readily be isolated by filtration, washing and drying. Excess bromine remaining after the completion of the reaction, may be reduced by a reducing agent such as sodium hydrogen sulfite. However, reduction treatment to bring the pH of the aqueous solution to a level of 7 or higher after the reduction is undesirable, since the catalyst will then become a solid or gelled hydroxide and will be included in the formed 4,4'-DBBP crystals. Of course, 4,4'-DBBP may be subjected to filtration without reducing bromine, and the filtrate may be recycled as it contains the catalyst and unreacted products.

According to the method of the present invention, it is possible to obtain 4,4'-DBBP in good yield with high selectivity in a short period of time and with easy control of the reaction.

Now, the present invention will be described in further detail with reference to Examples. However, it should be understood that the present invention is by no means restricted to such specific Examples.

EXAMPLES 1 to 12 and COMPARATIVE EXAMPLES 1 to 4

To a solution of BP (150 mmol) in the solvent as identified in Table 1 at a temperature of from 30 to 35° C., a predetermined amount of the catalyst as identified in Table 1 was added, or no catalyst was added. Then, bromine or its solution diluted with the solvent was dropwise added thereto over a period of one hour. Then, the mixture was heated to a predetermined temperature and heated for 5 hours. Other reaction conditions are also presented in Table 1. After completion of the reaction, the reaction mixture was cooled to 0° C., and the remaining bromine was treated by dropwise addition of a bromine-treating agent. As the bromine-treating agent, an aqueous sodium hydroxide solution was used in the no catalyst systems of Comparative Example 1 or 2, and an aqueous sodium hydrogen sulfite solution was used in other systems. The crystals in the reaction mixture were collected by filtration, washed with water and dried under vacuum at 46° C. The organic phase was separated from the filtrate and washed with water. The analyses of the components in the crystals and in the organic phase from the filtrate were conducted by gas chromatography, respectively. The results thereby obtained are shown in Table 2. The yield of 4,4'-DBBP is based on BP, and the distribution of the products are represented by the total amounts in the crystals and in the filtrates.

TABLE 1

| | Solvent | Initial concentration of BP (wt/vol %) | Dropwise added bromine Molar ratio relative to BP | Dropwise added bromine Concentration (wt %) | Catalyst (mol % relative to BP) | Aging temp. (°C.) |
|---|---|---|---|---|---|---|
| Example 1 | 1,2-Dichloroethane | 72 | 2.2 | 90 | SbCl$_3$(5.0) | 50 |
| Example 2 | 1,2-Dichloroethane | 36 | 2.2 | 90 | SbCl$_3$(5.0) | 50 |
| Example 3 | 1,2-Dichloroethane | 72 | 2.0 | 90 | SbCl$_3$(5.0) | 50 |
| Example 4 | 1,2-Dichloroethane | 72 | 2.6 | 90 | SbCl$_3$(5.0) | 50 |
| Example 5 | 1,2-Dichloroethane | 72 | 2.2 | 100 | SbCl$_3$(5.0) | 50 |
| Example 6 | 1,2-Dichloroethane | 72 | 2.2 | 70 | SbCl$_3$(5.0) | 50 |
| Example 7 | 1,2-Dichloroethane | 72 | 2.2 | 90 | SbCl$_3$(1.0) | 50 |
| Example 8 | Dichloromethane | 72 | 2.2 | 90 | SbCl$_3$(1.0) | 38 (refluxed) |
| Example 9 | 1,1,1-Trichloroethane | 72 | 2.2 | 90 | SbCl$_5$(1.0) | 50 |
| Example 10 | Chloroform | 72 | 2.2 | 90 | TiCl$_4$(1.0) | 50 |
| Example 11 | Chloroform | 72 | 2.2 | 90 | SnCl$_4$(1.0) | 50 |
| Example 12 | Chlorobenzene | 72 | 2.2 | 90 | ZnCl$_2$(1.0) | 50 |
| Comparative Example 1 | 1,2-Dichloroethane | 72 | 2.2 | 90 | None | 50 |
| Comparative Example 2 | Dichloromethane | 72 | 2.2 | 90 | None | 38 (refluxed) |
| Comparative Example 3 | 1,2-Dichloroethane | 72 | 2.2 | 90 | FeCl$_3$(1.0) | 50 |
| Comparative Example 4 | 1,2-Dichloroethane | 72 | 2.2 | 90 | AlCl$_3$(1.) | 50 |

TABLE 2

| | Distribution of products (mol %) | | | | | Yield of 4,4'-DBBP (mol %) |
|---|---|---|---|---|---|---|
| | BBP | 4,4'-DBBP | Other DBBP | TrBBP | TBBP | |
| Example 1 | 3.4 | 92.0 | 4.6 | 0.0 | 0.0 | 91.0 |
| Example 2 | 6.7 | 89.7 | 3.6 | 0.0 | 0.0 | 88.7 |
| Example 3 | 9.5 | 88.1 | 2.4 | 0.0 | 0.0 | 84.6 |
| Example 4 | 0.6 | 92.1 | 6.5 | 0.8 | 0.0 | 91.5 |
| Example 5 | 2.8 | 90.2 | 5.7 | 0.9 | 0.4 | 89.0 |
| Example 6 | 4.9 | 90.7 | 4.3 | 0.0 | 0.0 | 89.5 |
| Example 7 | 9.9 | 86.1 | 4.0 | 0.0 | 0.0 | 83.7 |
| Example 8 | 6.2 | 91.7 | 2.1 | 0.0 | 0.0 | 87.1 |

TABLE 2-continued

|  | Distribution of products (mol %) | | | | | Yield of 4,4'-DBBP (mol %) |
| --- | --- | --- | --- | --- | --- | --- |
|  | BBP | 4,4'-DBBP | Other DBBP | TrBBP | TBBP |  |
| Example 9 | 6.0 | 89.9 | 3.9 | 0.2 | 0.0 | 85.6 |
| Example 10 | 4.2 | 91.0 | 4.2 | 0.0 | 0.0 | 87.9 |
| Example 11 | 8.9 | 88.5 | 2.3 | 0.2 | 0.1 | 85.9 |
| Example 12 | 9.2 | 88.6 | 2.2 | 0.0 | 0.0 | 85.6 |
| Comparative Example 1 | 16.0 | 80.2 | 0.8 | 0.0 | 0.0 | 70.3 |
| Comparative Example 2 | 19.0 | 80.2 | 0.8 | 0.0 | 0.0 | 68.7 |
| Comparative Example 3 | 2.0 | 68.7 | 11.6 | 16.8 | 0.8 | 67.8 |
| Comparative Example 4 | 4.0 | 66.5 | 10.9 | 17.2 | 1.4 | 64.3 |

We claim:

1. A method for producing 4,4'-dibromobiphenyl, which comprises reacting biphenyl and from 2 to 3 mol times, relative to biphenyl, of bromine in a halogenated hydrocarbon solvent in the presence of a catalyst which is a metal selected from the group consisting of antimony, titanium, tin and zinc, or a halide, oxide, hydroxide, or inorganic or organic acid salt of said metal.

2. The method according to claim 1, wherein the catalyst is a halide, oxide, hydroxide, or inorganic or organic acid salt of antimony, titanium, tin or zinc.

3. The method according to claim 1, wherein the catalyst is antimony chloride, titanium chloride, tin chloride or zinc chloride.

4. The method according to claim 1, wherein the catalyst is used in an amount of from 0.1 to 10 mol % relative to biphenyl.

5. The method according to claim 1, wherein the solvent is chlorobenzene, o-dichlorobenzene, m-dichlorobenzene, dichloromethane, chloroform, carbon tetrachloride, 1,1-dichloroethane, 1,2-dichloroethane, 1,1,1-trichloroethane, 1,1,2-trichloroethane, 1,1,2,2-tetrachloroethane, tetrachloroethylene, 1-chloropropane, 2-chloropropane, 1,2-dichloropropane or 1,3-dichloropropane.

6. The method according to claim 1, wherein the initial concentration of biphenyl is from 10 to 100 wt/vol %.

7. The method according to claim 1, wherein the biphenyl solution is at temperature of from 0 to 40° C.

* * * * *